Feb. 2, 1954 F. W. ANDERSON Plant Pat. 1,248
NECTARINE TREE
Filed March 17, 1953
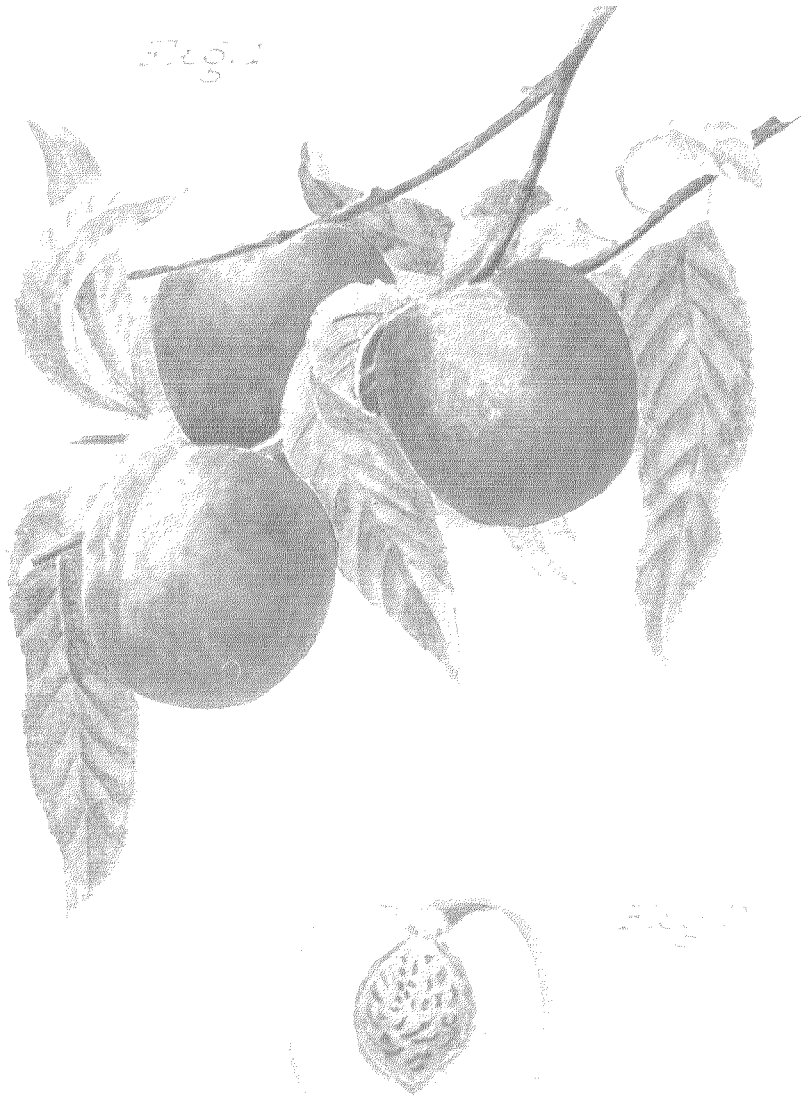
WITNESS
Addison F. Avery
INVENTOR
Frederic W. Anderson
Webster & Webster
ATTYS.

Patented Feb. 2, 1954

Plant Pat. 1,248

UNITED STATES PATENT OFFICE 1,248

NECTARINE TREE

Frederic W. Anderson, Merced, Calif.

Application March 17, 1953, Serial No. 343,006

1 Claim. (Cl. 47—62)

The present invention is directed to a new and distinct variety of nectarine tree which bears early ripening, yellow fleshed, semi-freestone fruit.

For a number of years I have conducted an extensive plant breeding program for the origination of commercially desirable nectarine trees; this program having been carried out in my experimental nursery and orchard near Le Grand, Merced County, California.

One of the primary aims of such program has been the production of a commercially acceptable early ripening nectarine having desirable market appeal and good shipping quality; these characteristics being present in the instant variety, and the major distinguishing characteristic of the same—as compared to other varieties—being a ripening period which is approximately one week earlier than the John Rivers nectarine (unpatented).

The new and distinct variety of nectarine tree here claimed was originated and asexually reproduced by me in my experimental nursery and orchard located as above, in the following manner:

I initially crossed the Le Grand nectarine (United States Plant Patent 549) with the John Rivers nectarine (unpatented), and the resulting seed were gathered and planted. As soon as the seedlings were large enough to obtain bud wood all were top-worked on mature root stock, and when such top workings bore fruit all were found to be white fleshed, clingstone nectarines.

From such white fleshed, clingstone nectarines—which were open-pollinated—seeds were gathered and planted, and of the resulting seedlings a number grew vigorously and were selected for subsequent observation; bud wood thereof having been subsequently top-worked on mature root stock. Of these latter top workings a majority retained the white fleshed, clingstone characteristic, but some were yellow fleshed and included the present variety. It was recognized as being of especial advantage, as it was not only yellow fleshed, but was semi-freestone, and had an extremely early ripening period, being approximately one week earlier than the John Rivers nectarine.

In further comparison with such John Rivers nectarine the present variety bears fruit which is yellow instead of white fleshed; is firmer fleshed; is more nearly freestone; is somewhat larger size, though remaining a relatively small fruit; and has more exterior red color.

Subsequent asexual reproductions of the present variety are found to carry forward the distinctive characteristics of the parent tree, as well as those of the initial top workings.

In the original drawings:

Fig. 1 is an elevation of three of the fruit of the present variety, together with twigs and leaves.

Fig. 2 is a sectional elevation of one of the fruit with the stone exposed.

Referring now more specifically to the pomological details of this new and distinct variety of nectarine tree, the following is an outline description thereof; all major color plate identifications being by reference to Marez and Paul Dictionary of Color:

Tree: Large; spreading; open; vase formed; productive; regular bearer.

Trunk: Medium size; medium texture.

Branches: Medium size; medium texture.

- *Color.*—Brown.
- *Lenticels.*—Medium number; medium size.

Leaves: Medium size. Average length, 6½ inches; average width, 1¾ inches. Lanceolate; medium thick; smooth.

- *Color.*—Top side—medium green (22–L–4); under side—lighter green (22–E–4).
- *Margin.*—Crenate.
- *Glands.*—Average number — four. Medium size; reniform. Position—usually two on petiole and two or three on blade. Stipules—none. Opposite and alternate.

Flower buds: Medium size; medium length; conic.

Flowers: Dates first and full bloom—about with Elberta peach. Medium early. Color—pink.

Fruit: Maturity when described—hard—June 18, 1952. Dates of first and last picking—June 15th to 22nd, 1952.

- *Size.*—Uniform; medium. Average diameter axially, 2¼ inches; transverse in suture plane, 2¼ inches.
- *Form.*—Uniform; globose.
- *Suture.*—Distinct; shallow; extends from base to beyond apex; has slight depression beyond pistil point.
- *Ventral surface.*—Rounded strongly; lips equal.
- *Cavity.*—Circular. Depth, ½ inch; breadth, ⅞ inch.
- *Base.*—Rounded.
- *Apex.*—Short; rounded.

Skin: Medium thick; medium texture.

- *Color.*—Yellow (11–K–8), shading in some areas to dull orange (4–J–11), and almost completely overspread and mottled with red (6–L–6 shading to 7–L–8).

*Tendency to crack.*—None.
*Down.*—Wanting.

Flesh:
*Color.*—Yellow (10–K–8), with red (3–J–8) near stone.
*Amygadalin.*—Moderate.
*Juice.*—Moderate.
*Texture.*—Firm; crisp; meaty; melting.
*Fibres.*—Few.
*Ripens.*—Evenly.
*Flavor.*—Subacid; delicate.
*Aroma.*—Distinct.
*Eating quality.*—Good to best.

Stone: Semi-free.
Size.—Small. Length, 1¼ inches; breadth, ⅝ inch; thickness, ½ inch.
*Form.*—Obovoid.
*Base.*—Straight.
*Hilum.*—Narrow.
*Apex.*—Acuminate.
*Sides.*—Equal.
*Surface.*—Irregularly furrowed near base; ridged toward apex; pitted throughout.
*Ridges.*—Rounded toward base.
*Pits.*—Elongated.
*Ventral edge.*—Thin.

*Dorsal edge.*—Full with narrow groove.
*Tendency to split.*—None.
*Color.*—Greyish brown (6–A–10, shading to 7–E–11).

Keeping quality: Good.
Use: Market; local; dessert; long distance shipping.
Shipping quality: Good.

The tree and its fruit herein described may vary in slight detail due to climatic and soil conditions under which the variety may be grown.

Having thus described the invention, I claim:

A new and distinct variety of nectarine tree, as described and illustrated, bearing relatively small, firm, yellow fleshed, semi-freestone fruit having yellow skin color, almost entirely overspread with red; characterized—in comparison with the John Rivers nectarine—by yellow instead of white flesh; ripening approximately one week earlier; slightly larger in fruit size; more exterior red color; firmer fleshed; and semi-freestone instead of clingstone.

FREDERIC W. ANDERSON.

No references cited.